United States Patent [19]
Levius

[11] Patent Number: 5,640,976
[45] Date of Patent: Jun. 24, 1997

[54] INCONTINENCE PLUG ANCHOR

[75] Inventor: Dezso K. Levius, Bloomington, Minn.

[73] Assignee: Iotek, Inc., Minneapolis, Minn.

[21] Appl. No.: 466,245

[22] Filed: Jun. 6, 1995

[51] Int. Cl.$^6$ .................................................. A61B 19/00
[52] U.S. Cl. .................. 128/885; 128/DIG. 25; 600/29
[58] Field of Search ..................... 128/830, 885, 128/DIG. 25, 887; 600/29–31

[56] References Cited

U.S. PATENT DOCUMENTS

| | | | |
|---|---|---|---|
| 2,324,520 | 7/1943 | Lamson | 128/DIG. 25 |
| 2,510,766 | 6/1950 | Surface | 128/DIG. 25 |
| 2,564,399 | 8/1951 | Franken | 128/DIG. 25 |
| 4,850,953 | 7/1989 | Haber et al. | 128/DIG. 25 |

*Primary Examiner*—Sam Rimell
*Attorney, Agent, or Firm*—Merchant, Gould, Smith, Edell, Welter & Schmidt

[57] ABSTRACT

A rolling incontinence plug partially or fully inserted within a urethra has an anchor to restrict its insertion into the urethra. The anchor is configured to be placed between a vestibule and labia minora for restricting insertion of the incontinence plug. The outer circumference of the anchor easily conforms to the shape of the vestibule and responds to varying pressure of the labia minora as the patient moves. Further, because the anchor naturally conforms to the vestibule, no additional artificial substances or devices are needed to secure the anchor.

5 Claims, 14 Drawing Sheets

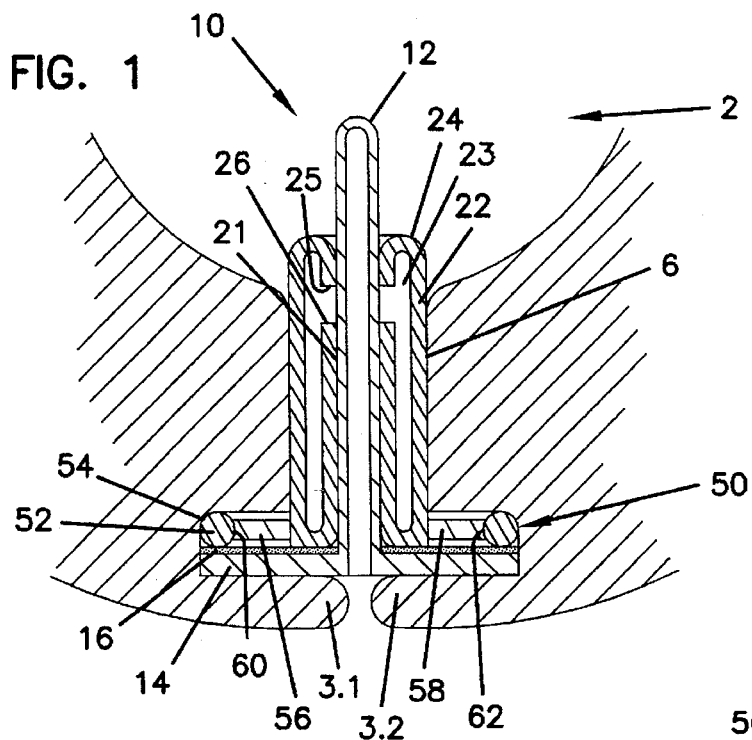
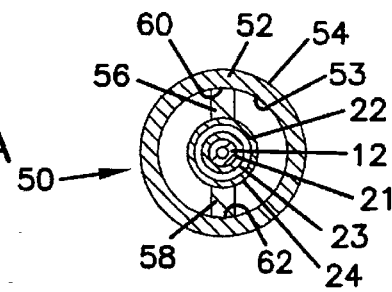
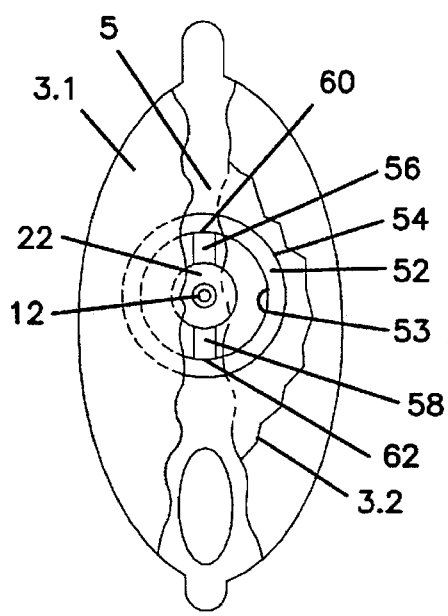
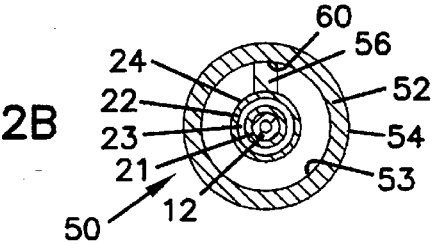
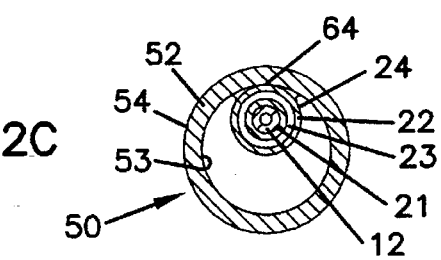
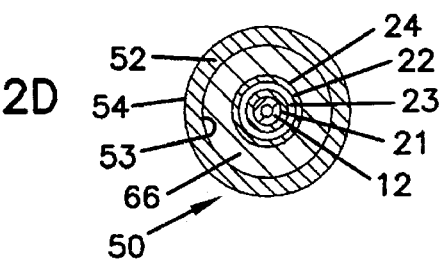

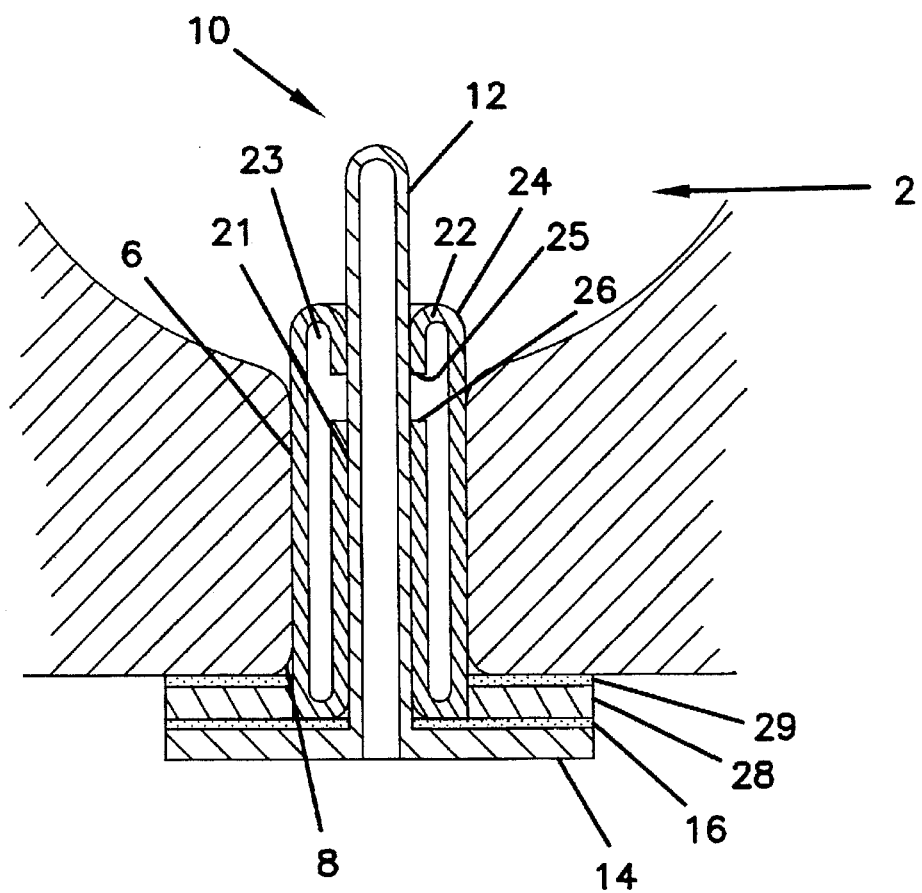

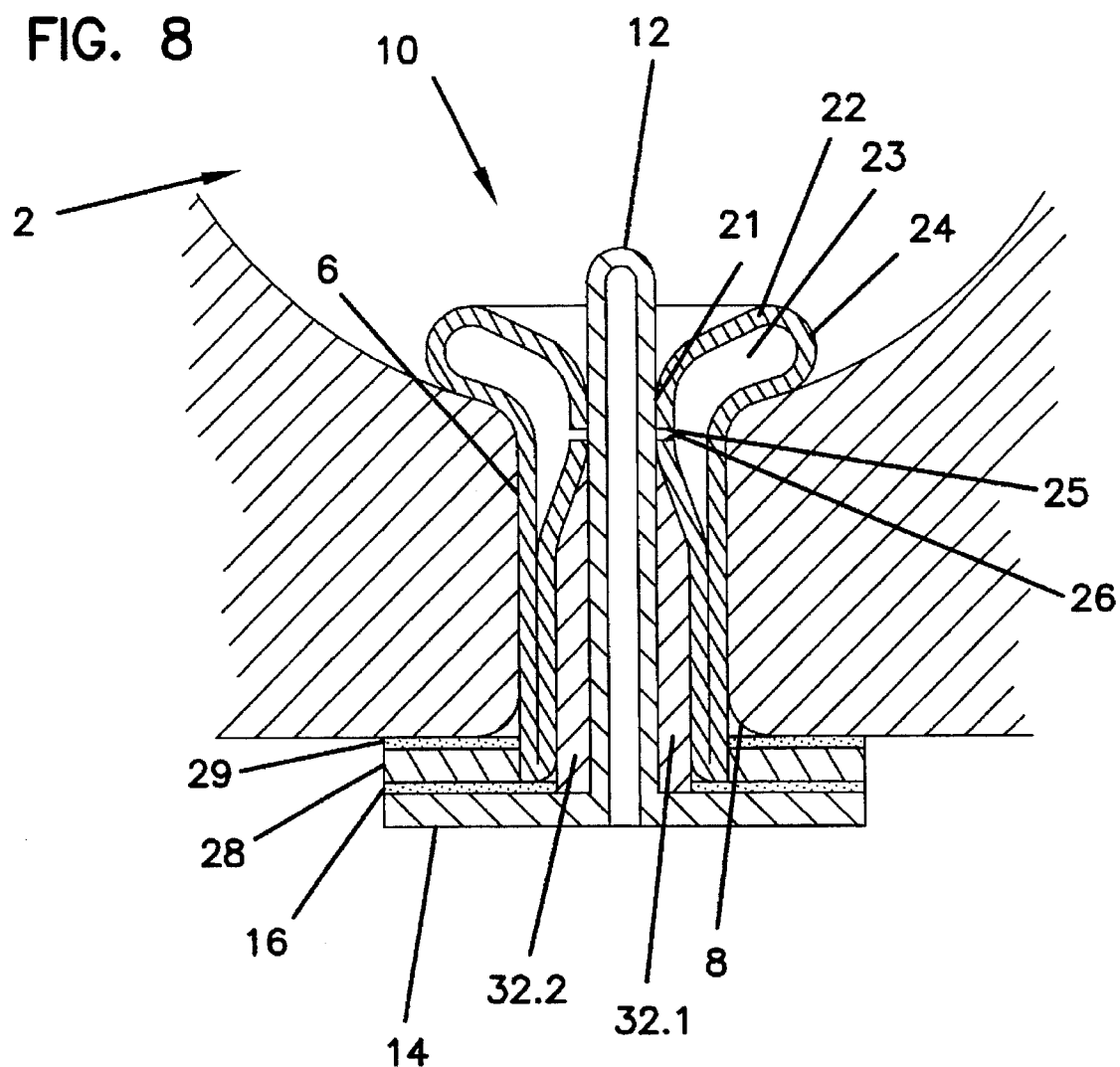

INCONTINENCE PLUG ANCHOR

CROSS REFERENCES

This application contains material found in concurrently filed, commonly assigned, co-pending U.S. patent application entitled "ROLLING INCONTINENCE PLUG", by inventors Deszo K. Levius and Arnold W. Thornton.

BACKGROUND OF THE INVENTION

Field of the Invention

This invention pertains to an incontinence control device. More particularly, this invention pertains to an anchor for a female incontinence plug.

Description of the Prior Art

The inability to deter the flow of urine from the bladder is a common phenomenon in women, particularly older women. Such inability to contain urine or other fluids is termed "incontinence". The urethra is the passage through which the bladder is normally emptied during urination. The urethra is surrounded by a muscle or sphincter (urethral wall) that voluntarily holds the urethra closed when normal individuals are not urinating. Patients suffering from incontinence experience a disruption in both their professional and recreational activities. Further, incontinence is detrimental to the self-esteem of the afflicted patients. One method of treating incontinence is to use a device that obstructs the urethra such that it prevents the uncontrollable flow of fluid from the bladder through the urethra.

Incontinence plugs for insertion into the urethra are known in the prior art. Examples of such devices include those shown in U.S. Pat. Nos. 5,090,424 and 5,080,006 and commonly assigned U.S. patent application Ser. No. 08/328, 331 filed Oct. 24, 1994, and entitled "INCONTINENCE DEVICE" by inventors Robert E. Buuck and Dezso K. Levius. The '331 application utilizes a sleeve for initial insertion into the urethra. The incontinence plug is then passed through the sleeve such that the distal end of the plug does not come in contact with the entrance to the urethra. By not contacting the entrance to the urethra, the plug will not transport pathogens or bacteria from the urethral entrance or meatus to the bladder.

For a female incontinence device to be effective and to be used by a large number of patients, the design should accomplish several objectives. The device should restore continence to an acceptable level in a majority of patients for whom it may be prescribed. The incontinence device must be used with a minimum of complications. The incontinence device should be insertable into the urethra by the patient with a minimum of physical and social discomfort. Also, the incontinence device must be designed in such a manner and with materials acceptable to the Food and Drug Administration, so that the device can be produced, packaged and sterilized at low cost.

Most prior art involve devices that are pushed along the inside of the urethra, thereby rubbing against the urethral wall until fully inserted. The rubbing along the urethral wall by the incontinence device as it is being pushed through the urethra can cause trauma to the vessel. Further, pushing an incontinence device through the urethra can result in bacteria or other pathogens being transported from the urethral entrance along the urethra and toward or into the bladder.

These prior art devices that are inserted at least partially into the urethra typically use some method to restrict the plug insertion into the urethra. Such methods include using an adhesive to secure a portion of the incontinence plug to the body area of the patient surrounding the urethral entrance, called a vestibule. Adhesives used on the body can be messy and uncomfortable for the patient, especially during removal of the incontinence plug. Other methods include utilizing a sufficiently wide, solid material at the end of the incontinence plug, that abuts the vestibule and restricts insertion of the plug into the urethra. Such solid material, however, does not conform to the shape of the vestibule as the patient moves, and will buckle and create a spring-like force which is uncomfortable for the patient.

While the aforementioned devices advance treatment of incontinence, incontinence plugs having anchors that conform to the shape of the vestibule without an abundance of material are desired. Further, incontinence plugs having anchors that do not utilize uncomfortable adhesives against the body are desired. It is an object of the present invention to provide an improved design of an anchor for an incontinence plug that does not rely on adhesives to secure the incontinence plug to the body and that substantially reduces the amount of material used to secure the incontinence plugs.

SUMMARY OF THE INVENTION

In accordance with one aspect of the invention, a rolling incontinence plug is provided. The plug includes a sealing member for preventing leakage of fluid from the bladder. The sealing member has an attached anchor member for anchoring the plug between the patient's vestibule and labia minora.

In one aspect of the invention, the anchor member has two ribs connected to the sealing member. The ribs are narrow and thin. In another aspect of the invention, the anchor member has only one rib connected to the sealing member. In yet another aspect of the invention, the anchor member has a thin mass surrounding the sealing member for connecting the anchor member thereto. Finally, in a further aspect of the invention, the anchor member does not have any connecting material and is bonded directly to the sealing member.

Regardless of the embodiment of the anchor member utilized, the anchor member is inserted between the vestibule and labia minora of the patient. The outer circumference of the anchor member easily conforms to the shape of the vestibule and varying pressure of the labia minora as the patient moves, without producing thick, buckled material that creates an added spring-like pressure and discomfort to the patient.

While the present invention is described in association with particular shapes of an anchor member, the invention is not limited in the type of shape that will provide an effective anchor in accordance with the principles of the invention. Further, while the present invention has been described with reference to particular types of connections between the anchor member and the sealing member of an incontinence plug, it is obvious that any type of connection that does not produce thick, solid material that buckles upon movement by the patient, will provide an effective connection in accordance with this invention. Although the anchor member is described as being attached to the sealing member of a plug, the anchor member could be attached to any part of the plug not inserted into the urethra. Finally, although the invention is described as being used within an urethra to prevent uncontrollable flow of fluid from the bladder, it will be apparent that the invention could be utilized to anchor other sealing devices in passageways such as, for example, a rectum or a vagina to prevent the uncontrollable flow of fluid or other substances. These and other features of the invention will become apparent to those skilled in the art upon more detailed description of the preferred embodiments of the invention.

BRIEF DESCRIPTION OF THE DRAWINGS

FIG. 1 is a diagrammatic cross-sectional side view of a preferred embodiment of a rolling incontinence plug in its fully inserted position within a urethra;

FIGS. 2A through 2D are diagrammatic top-sectional views of various embodiments of an anchor member as shown in cross-sectional view in FIG. 1 abutting a vestibule and a urethral entrance;

FIG. 3 is a diagrammatic bottom view of the anchor member of FIG. 2A, having a bottom sectional view of the incontinence plug of FIG. 1, installed in the external genitalia of a human female;

FIG. 6 is a diagrammatic cross-sectional side view of an alternative embodiment of a rolling incontinence plug according to the present invention in its fully inserted position within a urethra;

FIG. 8 is a diagrammatic cross-sectional side view of an alternative embodiment of a rolling incontinence plug according to the present invention in its fully inserted position in a urethra where the incontinence plug utilizes sleeve members to mold the incontinence plug into sealing engagement with a bladder neck and a urethral wall;

DETAILED DESCRIPTION OF THE PREFERRED EMBODIMENT

Figure 4:
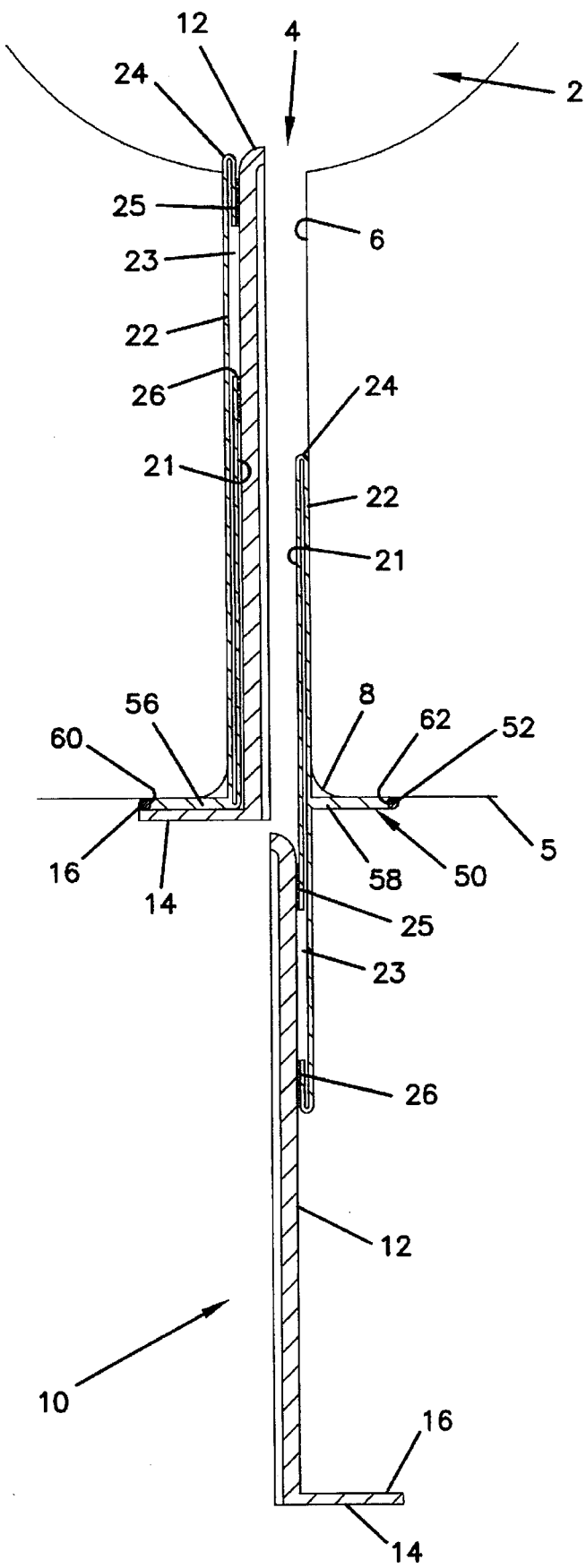
FIG. 4 is a split cross-sectional side view of a rolling incontinence plug showing the left side of the plug in its fully inserted position and the right side of the plug in an initial insertion position.

With reference now to the various drawing figures in which identical elements are numbered identically throughout, a description of the preferred embodiments of the present invention will now be provided.

Referring to FIG. 1, a preferred embodiment of a rolling incontinence plug 10 is shown in a diagrammatic cross-sectional side view. The plug 10 has an elongated, substantially cylindrical, hollow stem 12 with a radially extending flange 14 at a proximal end. The flange 14 preferably has an adhesive layer 16 covering an upper side of the flange 14. In this preferred embodiment, a distal end of the stem 12 is rounded and closed. The stem 12 is positioned inside an axial hole defined by opposing surfaces 21 of an exterior surface 24 of a sealing member 22. The sealing member 22 is substantially shaped like an inverted tube and the exterior surface 24 sealably engages a urethral wall 6. In this preferred embodiment, the sealing member 22 is fixedly attached to the stem 12 at inverted tube ends 25 and 26. The inverted tube ends 25 and 26 are attached by any suitable method, such as bonding, along the outer circumference of the stem 12 where the inverted tube ends 25 and 26 contact the stem 12. The sealing member 22 has an interior hollow area 23 that is filled with a deformable substance. In the preferred embodiment, the deformable substance used is saline. It will be apparent to those in the art that any deformable, non-toxic substance could be used. The exterior surface 24 of the sealing member 22 is secured to an anchor member 50 in the preferred embodiment. When the plug 10 is fully inserted, the anchor member 50 is anchored between a vestibule 5 and a pair of labia minora 3.1 and 3.2 of the patient and the flange 14 is secured to the anchor member 50 by the adhesive layer 16. It will be obvious to those skilled in the art that the flange 14 could be secured to the anchor member 50 by other means, such as, for example, a snapping mechanism between the flange 14 and the anchor member 50. In addition, as will be apparent to those skilled in the art, the flange 14 itself could be an anchor member of the same or similar configuration as described with reference to the embodiments of the anchor member 50.

Various embodiments of the anchor member 50 are shown in FIGS. 2A-2D. In the preferred embodiment, the anchor member 50 has a flexible outer peripheral member 52 with an exterior surface 54. The peripheral member 52 is substantially in the shape of a tubular ring which preferably can be made of deformable rubber. However, any other material having like characteristics can be utilized. Further, it will be apparent that the rubber peripheral member 52 can be solid or hollow with the hollow embodiment being filled with air or with a deformable material or fluid. The exterior surface 54 of the peripheral member 52 has an inner area 53 defining an inner circumference of the peripheral member 52. As will be apparent to those in the art, and as shown in FIGS. 2A-2D, the exterior surface 24 of the sealing member 22 can be connected to the flexible peripheral member 52 in a variety of ways. In FIG. 2A, two pliable connecting ribs 56 and 58 attach to both the exterior surface 24 of the sealing member 22 and the exterior surface 54 of the peripheral member 52. In the preferred embodiment shown in FIG. 2A, the ribs 56 and 58 attach to the exterior surface 54 at points 60 and 62, respectively, along the inner area 53 of the peripheral member 52. FIG. 2B is an alternative embodiment of FIG. 2A wherein the peripheral member 52 is connected to the sealing member 22 by only one pliable connecting rib 56. In FIG. 2C, the sealing member 22 is affixed directly to the exterior surface 54 of the peripheral member 52 at point 64 along the inner area 53 of the peripheral member 52. Finally, FIG. 2D shows a substantially planar, connecting body 66, surrounding and attached to the sealing member exterior surface 24, such that the sealing member 22 extends axially through the connecting body 66. The connecting body 66 extends radially outwardly from the sealing member 22 and attaches to the peripheral member exterior surface 54 along the entire inner circumference defined by the inner area 53 of the peripheral member 52. The connecting ribs 56 and 58 and the connecting body 66 are thin and pliable, and can be formed of the same material as the peripheral member 52, although reduced in thickness. Upon a description of the operation, it will be apparent to those in the art that the overriding criteria for any connecting rib or body between the sealing member 22 and the peripheral member 52, are pliability and reduced material.

Referring to FIG. 3, a diagrammatic bottom view of the anchor member 50, shown in FIG. 2A, is shown installed in the external genitalia of a human female. FIG. 3 shows one side of the anchor member 50 covered by one of the pair of labia minora 3.1, as indicated by the dashed-line representation of the peripheral member 52. The opposing side of the anchor member is shown with the other of the pair of labia minora 3.2 cut away, as indicated by the dashed-line representation of the labia minora 3.2. In the preferred embodiment, the anchor member 50 is configured to conform to the vestibule 5, while being naturally anchored against the vestibule 5 by the labia minora 3.1 and 3.2.

As shown in FIG. 1, the sealing member 22 is inserted into a passageway referred to as a urethra 4. The urethra 4 is defined by the aforementioned urethral wall 6. One end of the urethra 4 connects to a bladder 2. The opposite end of the urethra is a urethral entrance 8 through which the rolling incontinence plug 10 is initially inserted.

FIG. 4 shows a split cross-sectional view of the preferred embodiment of the rolling incontinence plug 10, shown in diagrammatic form in FIG. 1, with the right side of the plug 10 being only partially inserted into the urethra 4 and the left side of the plug being fully inserted into the urethra 4 and the bladder 2. As shown in the partially inserted view (on the right), the distal end of the stem 12 is positioned within the axial hole of the sealing member 22 prior to insertion.

Operation

Figure 5:
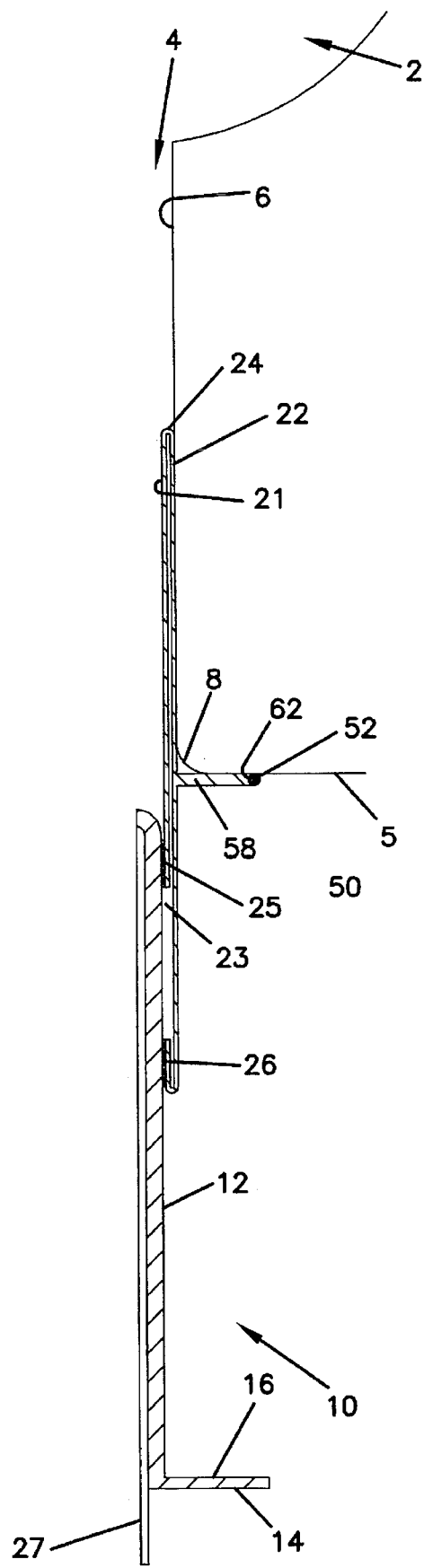
FIG. 5 is a split step-by-step cross-sectional side view of the rolling incontinence plug shown in FIG. 4 being inserted into a urethra.

FIG. 5 shows a split cross-sectional view of the step-by-step insertion from right to left of the rolling incontinence plug 10, shown in diagrammatic form in FIG. 1, into the urethra 4. For ease of readability, only the first step shown in FIG. 5 is numbered, it being apparent that each successive step would have the same reference numbering. The plug 10 can be initially inserted via an insertion applicator (not shown) or by gripping the peripheral member 52 of the anchor member 50 and pushing a distal tip of the sealing member 22 into the urethral entrance 8. Force applied to opposing edges of the peripheral member 52 will cause the anchor member 50 to bend into a substantially oval shape. The anchor member 50 is sufficiently flexible to allow easy placement between the vestibule 5 and the labia minora 3.1 and 3.2. Once the plug 10 is initially inserted into the urethra 4 and the anchor member 50 is placed between the vestibule 5 and the labia minora 3.1 and 3.2, the force is released and the anchor member 50 is naturally anchored between the labia minora 3.1 and 3.2 and the vestibule 5, conforming to the shape of the vestibule 5 in response to the pressure applied by the labia minora 3.1 and 3.2. As the patient moves, the anchor member 50 conforms to the changes in pressure from the labia minora 3.1 and 3.2, without producing any thick, buckled material or discomfort to the patient.

Upon initial insertion of the plug 10 into the urethra 4, as shown on the far right side of FIG. 5, a longitudinal force is applied to the stem 12 to advance the stem 12 through the urethra 4 toward the bladder 2. As the stem 12 is advanced, the stem attachments to the inverted tube ends 25 and 26 force the sealing member 22 to roll along the urethral wall 6. Prior to insertion, a stiffening rod 27 (shown in FIG. 5) can be placed through the hollow stem 12 to provide sufficient stiffness to the stem 12 to permit the longitudinal force to advance the stem 12 through the sealing member 22, thereby causing the sealing member 22 to roll along the urethral wall 6. It will be apparent to those skilled in the art that the inverted tube ends 25 and 26 must be attached to the stem 12 at a location that allows the sealing member 22 to continue rolling along the urethral wall 6 until the plug 10 is fully inserted with the flange 14 being in communication with the anchor member 50. Once the flange 14 has advanced to communication with the anchor member 50, the stem 12 has fully advanced into the bladder 2 and the sealing member 22 has rolled to the neck of the bladder 2. The adhesive layer 16 on the flange 14 secures the flange 14 to the anchor member 50, thereby securing the plug 10 in its fully inserted position. The far left step shown in FIG. 5 shows a split view of the rolling incontinence plug 10 in its fully inserted position.

Figure 18:
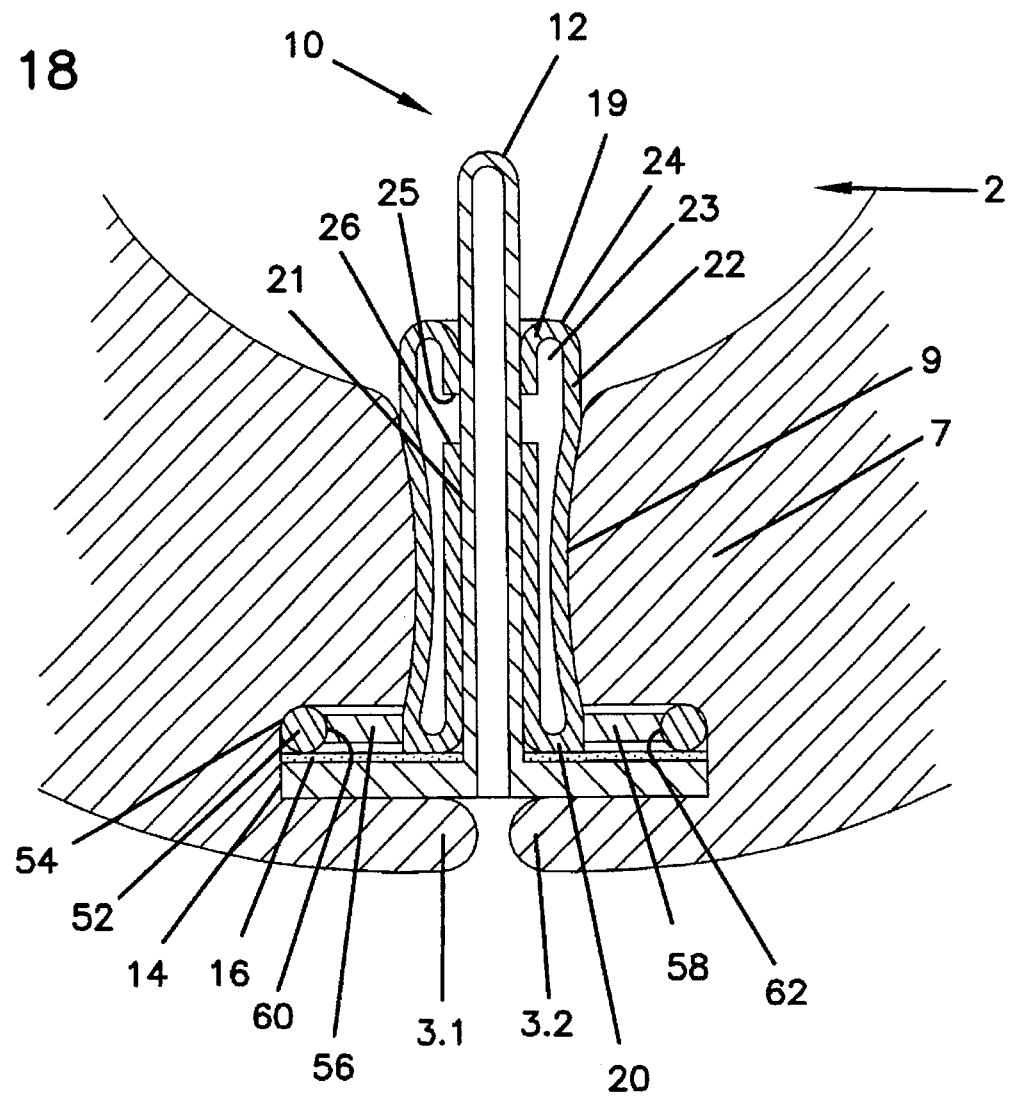
FIG. 18 is a diagrammatic cross-sectional side view of a preferred embodiment of a rolling incontinence plug in its fully inserted position within a urethra being naturally deformed by sphincter muscles surrounding the urethra.

While the anchor member 50 is used to secure the plug 10 and restrict further insertion into the urethra 4, it is expected that most patients will have a natural, internal anchor as shown in FIG. 18. Although incontinence is caused when sphincter muscles 7 relax and no longer automatically close the urethra, some amount of pressure by the sphincter muscles 7 may still occur. As shown in FIG. 18, even a small amount of pressure by the sphincter muscles 7 will cause inward curvature of the plug 10 at sphincter pressure point 9. The inward curvature will cause a distal end 19 and a proximal end 20 of the sealing member 22 to naturally expand. Such deformation of the plug 10 will create a natural internal anchor for the plug 10 at the expanded distal and proximal ends 19 and 20 respectively, of the plug 10. The expanded distal end 19 will prevent involuntary dislodging of the plug 10. The expanded proximal end 20 will restrict involuntary insertion of the plug 10 into the urethra.

When the plug 10 is removed, the flange 14 is severed from the anchor member 50 and the stem 12 is pulled out of the bladder 2 and the urethra 4, which causes the sealing member 22 to roll down the urethral wall 6 toward the urethral entrance 8. Both the insertion and removal of the rolling incontinence plug 10 shown in FIG. 5 utilize the friction between the exterior surface 24 of the sealing member 22 and the urethral wall 6 to aid the rolling action of the sealing member 22 along the urethral wall 6. The rolling action of the sealing member 22 along the urethral wall 6 reduces trauma, which is often caused by rubbing against the urethral wall 6. In addition, the rolling action reduces the pathogens and bacteria transported through the urethra 4 because the sealing member 22 does not slide through the urethra 4.

Alternative Embodiments

FIGS. 1 and 6 through 18, are not drawn to scale. Rather, these figures are diagrammatically drawn for ease of reference. For example, the stem referenced as 12 in FIGS. 1, 6–11, and 18, and referenced as 112 in FIGS. 12–17, may be sized to be twice the length of the urethra to aid in pre-insertion of the device.

Referring to FIG. 6, an alternative embodiment of the preferred rolling incontinence plug 10 of FIG. 1 is shown. The plug 10 in FIG. 6 has one modification to the plug 10 shown in FIG. 1. The plug 10 in FIG. 6 utilizes a flange 28 attached to the sealing member 22, rather than the preferred anchor member 50 shown in FIGS. 1–3. The flange 28 has an adhesive layer 29 covering an upper side of the flange 28 for securing the flange 28 against the vestibule 5. Although the alternative embodiments hereinafter described are shown using a flange 28 attached to the sealing member 22, it will be apparent that each alternative embodiment could utilize an anchor member attached to the sealing member 22 as described with reference to FIGS. 1 through 3.

Figure 7A:
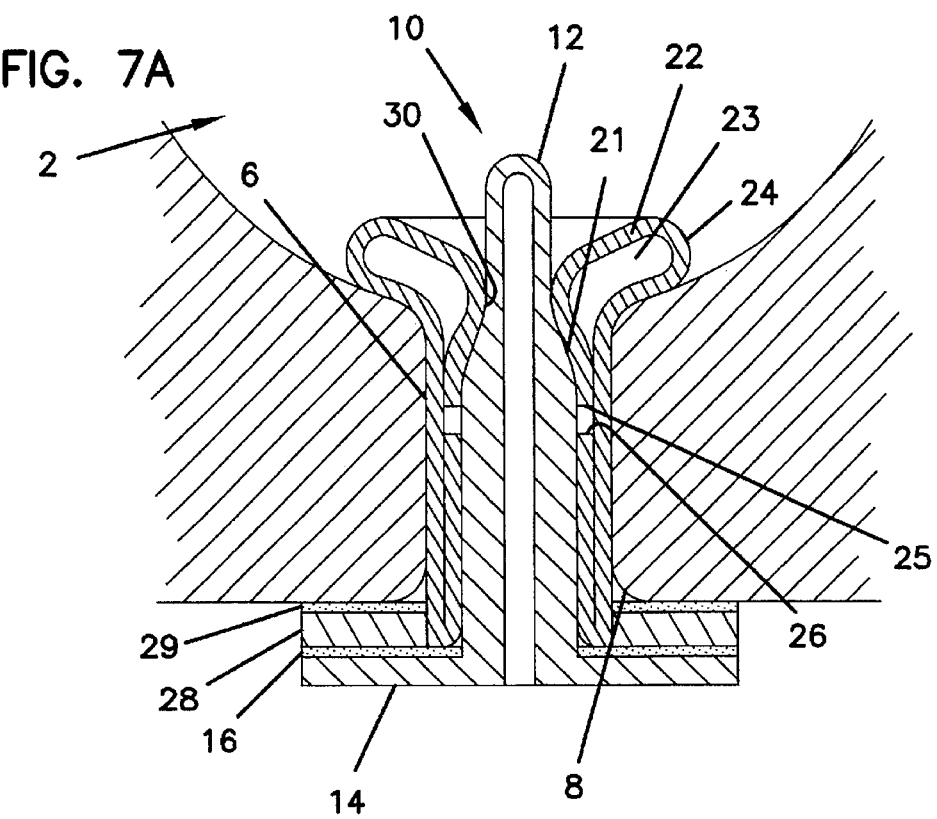
FIG. 7A is a diagrammatic cross-sectional side view of an alternative embodiment of a rolling incontinence plug according to the present invention in its fully inserted position in a urethra where a portion of the incontinence plug is shaped to mold the plug into sealing engagement with a bladder neck and a urethral wall.
Figure 7B:
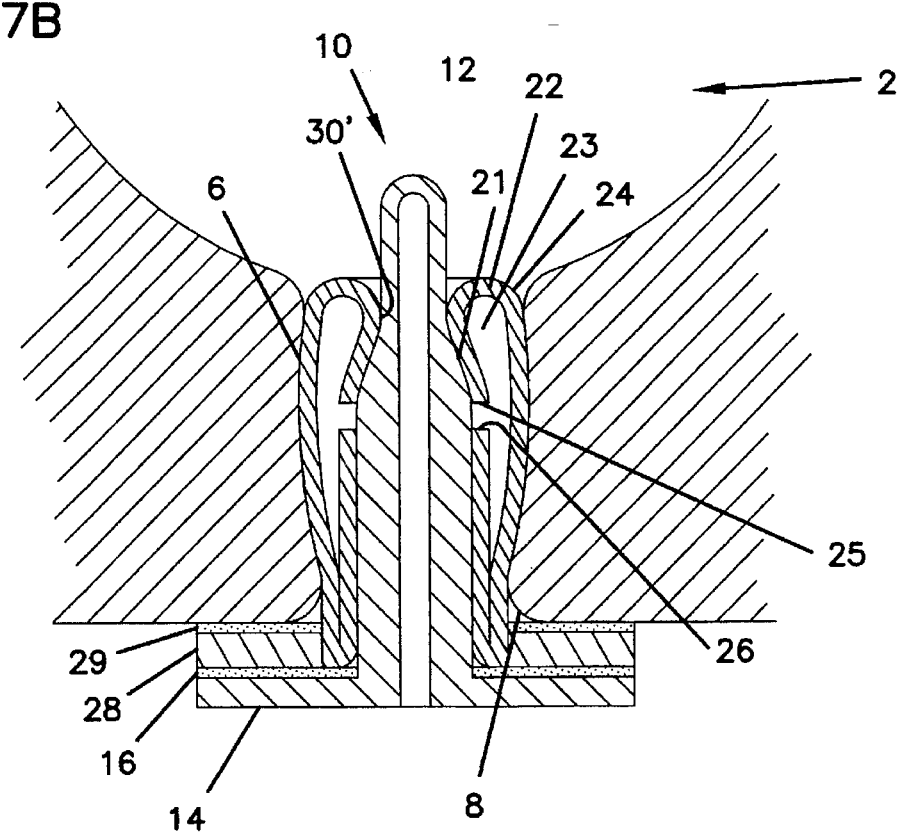
FIG. 7B is a diagrammatic cross-sectional side view of an alternative embodiment of the rolling incontinence plug shown in FIG. 7A in its fully inserted position where a portion of the incontinence plug is shaped to mold the incontinence plug into sealing engagement with the urethral wall.

FIGS. 7A and 7B show alternative embodiments for the present invention providing various configurations of the stem 12 to create a leak-proof seal between the sealing member 22 and the urethral wall 6 and the bladder 2. FIG. 7A shows a fully inserted plug 10 where the stem 12 tapers outwardly and downwardly toward the flange 14. The diameter of the tapered portion of the stem 12 is greater than the diameter of the distal end of the stem 12. The tapering begins at a location 30 between the proximal and the distal end of the stem 12 such that when the plug 10 is fully inserted, the sealing member 22 is sealably pressed against a portion of the urethral wall 6 and is partially pressed into the bladder 2.

FIG. 7B is a slight modification of the embodiment shown in FIG. 7A. The stem 12 in FIG. 7B begins tapering at a location 30' between the distal end and the proximal end such that when the plug 10 is fully inserted, the sealing member 22 is sealably pressed against the urethral wall 6 and is entirely within the urethra 4.

FIG. 8 shows an alternative embodiment of the present invention using sleeve members 32.1 and 32.2 to sealably press the sealing member 22 against the urethral wall 6 and into the bladder 2, thereby preventing leakage of fluid from the bladder 2. FIG. 8 shows sleeve members 32.1 and 32.2 extending upwardly from the flange 14 along the outer circumference of the stem 12 where the inverted tube ends 25 and 26 contact the stem 12. The distal ends of the sleeve members 32.1 and 32.2 taper outwardly (toward the sealing member 22 when the plug 10 is inserted) and downwardly toward the flange 14. This embodiment presses the sealing member 22 against the urethral wall 6 and into the bladder 2. The sleeve members 32.1 and 32.2 communicate such that combined, they surround the stem 12. As will be obvious to those skilled in the art, the sleeve members could comprise various configurations. Like the embodiment shown in FIG. 7B, the sleeve members could be configured to press the sealing member 22 into the urethral wall 6 entirely within the urethra 4 and not extending into the bladder 2. It will be further apparent to those in the art that the sleeve members may either partially or entirely surround the stem 12. As will also be obvious to those in the art, the sleeve members could comprise two or more sleeve members as shown and described, or only one sleeve member that entirely or partially surrounds the stem 12.

Figure 9:
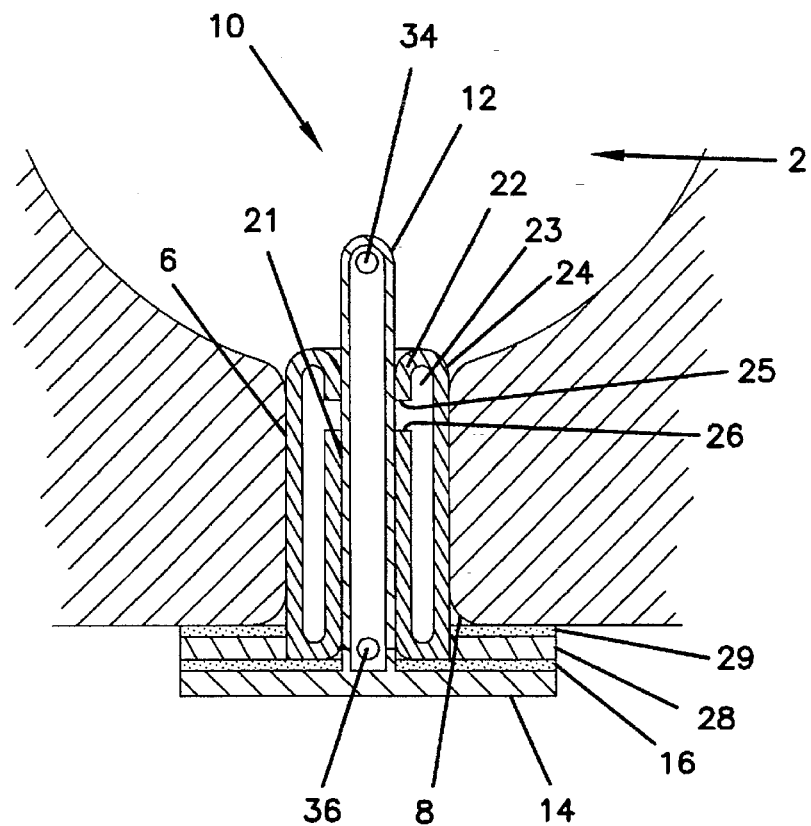
FIG. 9 is a diagrammatic cross-sectional side view of an alternative embodiment of a rolling incontinence plug according to the present invention in its fully inserted position within a urethra where the incontinence plug allows selective depletion of fluid using an inlet port and an outlet port in the plug.
Figure 10:
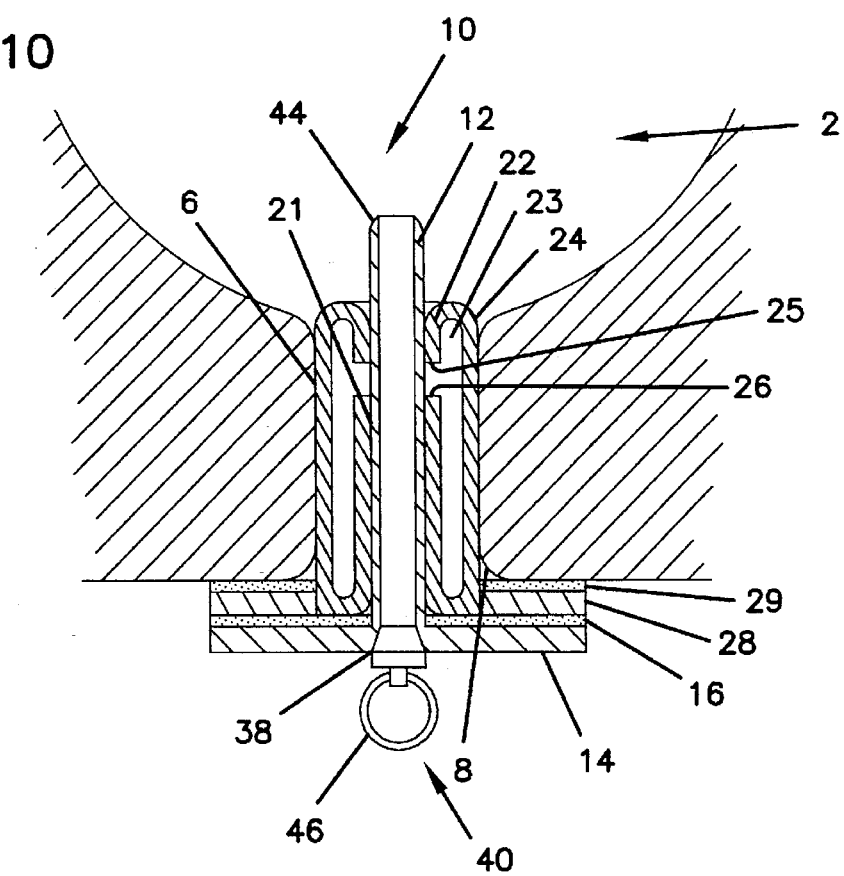
FIG. 10 is a diagrammatic cross-sectional side view of an alternative embodiment of the rolling incontinence plug, similar to that of FIG. 9 where the plug allows selective depletion of fluid, having an open passageway with a removable blocking plug.

FIG. 9 shows an alternative embodiment of the present invention offering the patient the added feature of selectively releasing fluid from the bladder 2 without removing the plug 10. The plug 10 is configured substantially the same as the embodiment shown in FIG. 6. However, the stem 12 must be hollow and has an inlet port 34 near the distal end and an outlet port 36 near the proximal end. The inlet port 34 receives fluid from the bladder 2 and the outlet port 36 releases the fluid received in the inlet port 34. The plug 10 is configured such that when fully inserted as shown in FIG. 10, the sealing member 22 is positioned around the hollow stem 12 to block the outlet port 36. The patient can selectively release fluid by moving the stem 12 and thereby rolling the sealing member 22 to a position whereby the sealing member 22 does not block the inlet port 34 or the outlet port 36. This allows fluid to flow through the inlet port 34 and out of the outlet port 36. Once the fluid depletion is complete, the patient simply advances the hollow stem 12 back into its fully inserted position, causing the sealing member 22 to roll back into the position of blocking the outlet port 36 of the stem 12. It will be obvious to those skilled in the art that the plug 10 could also be configured such that the sealing member 22 blocks the inlet port 34 while in the fully inserted position. Movement of the stem 12 would roll the sealing member 22 and thereby allow the inlet port to receive fluid from the bladder 2 which would then be released through the outlet port 36. It will also be obvious to those skilled in the art that, rather than utilizing an inlet port as shown in FIG. 9, the distal end of the stem 12 could be open, allowing fluid from the bladder 2 to flow through the stem 12.

FIG. 10 is an alternative embodiment of the present invention utilizing the added feature of selective release of fluid from the bladder 2 as described with reference to FIG. 9. In the embodiment shown in FIG. 10, the stem 12 is hollow. The flange 14 has an opening 38 where the hollow stem 12 is attached. A blocking plug or valve 40 is inserted into the flange opening 38 to prevent fluid from escaping from the hollow stem 12. The blocking plug 40 as shown in FIG. 10 has a rounded handle 46 for pulling the blocking plug 40 out of the hollow stem 12. The distal end of the hollow stem 12 is not closed as shown in previous embodiments. Rather, the distal end is open allowing fluid from the bladder 2 to freely flow into the hollow stem 12. The distal end has rounded edges 44, to aid in the insertion of the plug 10. Obviously, the distal end could be closed and the stem could have an inlet port on the side of the stem 12, rather than an open distal end, for receiving bladder fluid. As will be apparent to those skilled in the art, the blocking plug 40 can assume various configurations.

Figure 11:
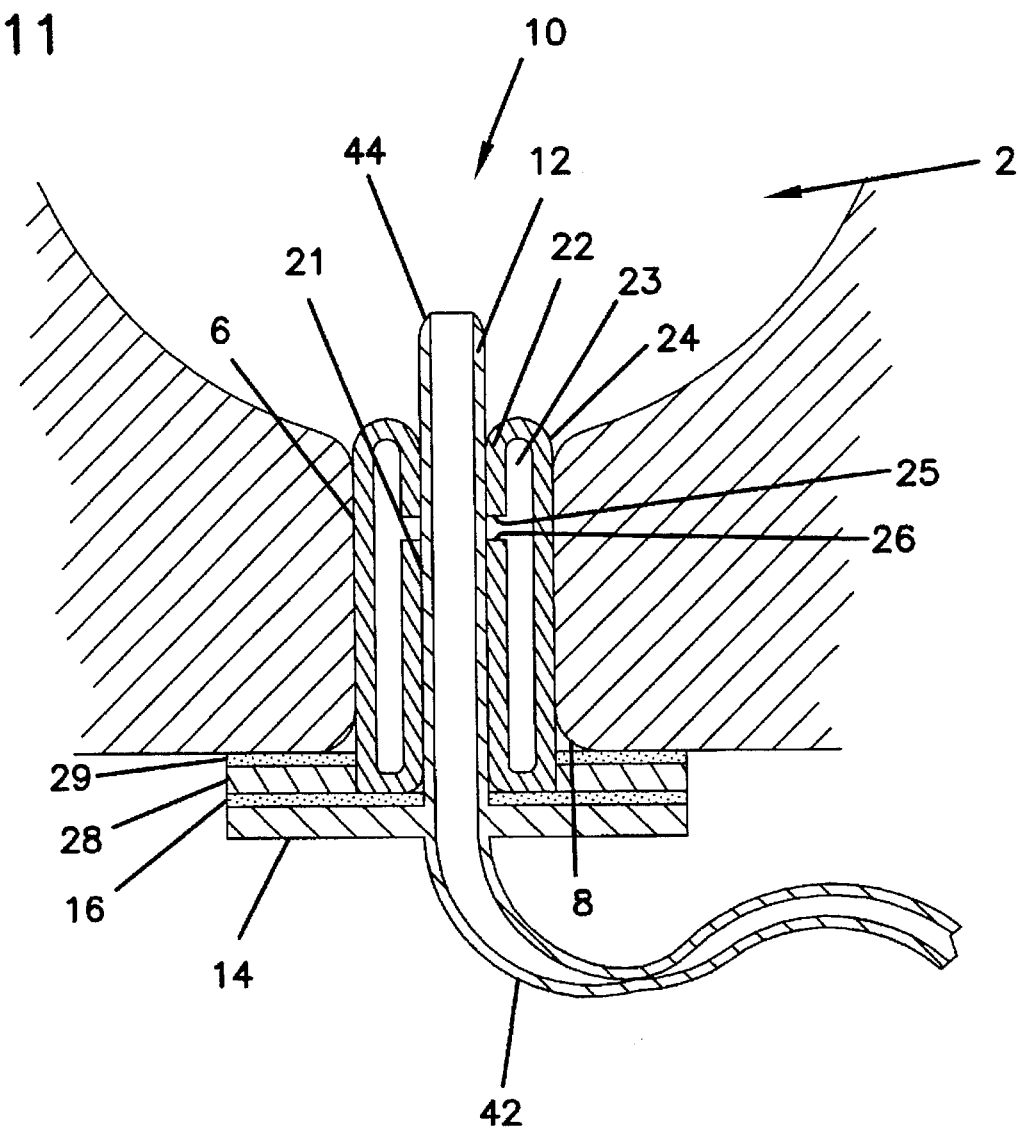
FIG. 11 is a diagrammatic cross-sectional side view of an alternative embodiment of the rolling incontinence plug, similar to that of FIG. 9 where the plug allows selective depletion of fluid, showing a plug extension kinked or otherwise clamped to allow selective depletion of fluid.

FIG. 11 is another embodiment of the present invention providing for the selective release of fluid from the bladder 2. In the embodiment shown in FIG. 11, the stem 12 is hollow. The flange 14 has an opening 38 where the hollow stem 12 is attached to the flange 14. A hollow stem extension 42 is connected to the flange opening 38 and extends beyond the flange 14. The stem extension 42 is made of deformable material that can be kinked to prevent leakage of fluid from the hollow stem 12. The patient can selectively un-kink the stem extension to release fluid from the bladder 2 and then kink the stem extension 42 again to prevent leakage. As will be apparent to those skilled in the art, other clamping devices that restrict fluid flow can be utilized with the stem extension 42 to prevent leakage.

FIGS. 12 through 17 show alternative embodiments of the embodiments described above. The significant difference resides in the configuration of the sealing member 22.

Figure 12:
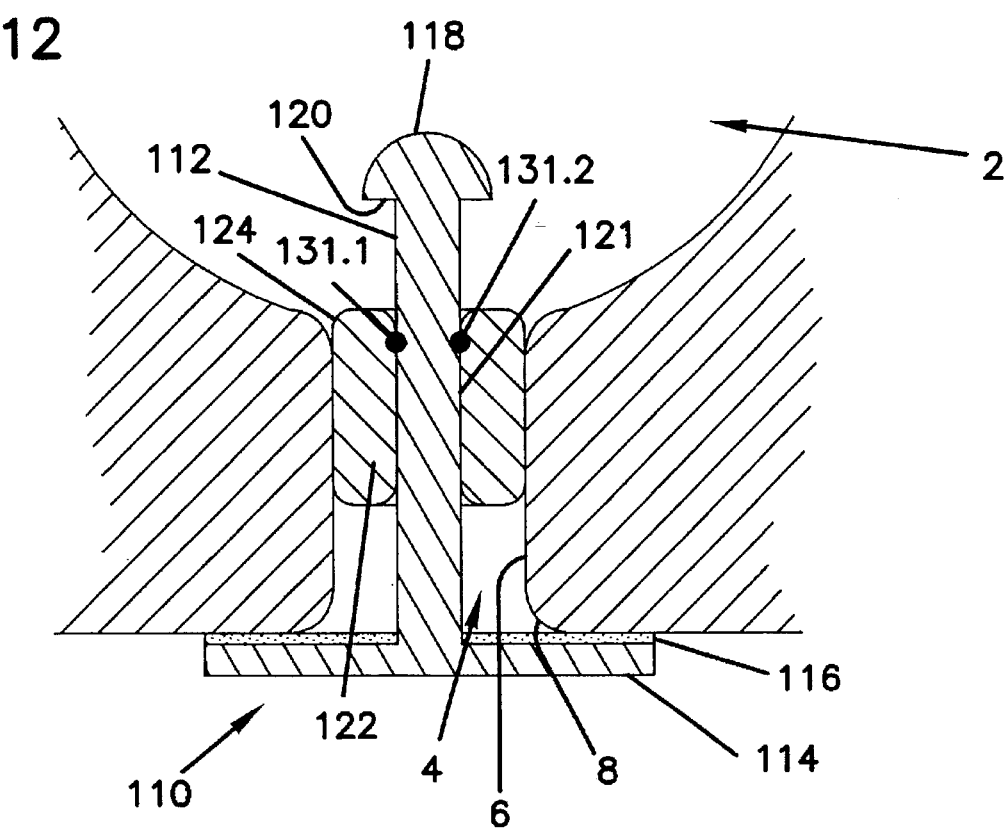
FIG. 12 is a diagrammatic cross-sectional side view of an alternative embodiment of the rolling incontinence plug according to the present invention in its fully inserted position, within a urethra.

Referring to FIG. 12, a rolling incontinence plug 110 is shown having an elongated substantially cylindrical, hollow stem 112 with a radially extending flange 114 at a proximal end. The flange 114 has an adhesive layer 116 covering an upper side of the flange 114 for securing the plug 110 to the vestibule 5. At a distal end of the stem 112, a hemispherical dome 118 having a radially extended bottom surface 120 is attached to the stem 112 to prevent the sealing member 122 from rolling off the end of the stem 122. The stem 112 is disposed within an axial hole defined by opposing surfaces 121 of an exterior surface 124 of a sealing member 122. The sealing member 122 is substantially torroidal in shape and the diameter of the hole in the sealing member 122 is sized to frictionally engage the stem 112 positioned therethrough. The sealing member 122, shown as a solid in FIGS. 12–17, can be hollow and filled with a deformable substance. The exterior surface 124 of the sealing member 122 is made of a material that can frictionally engage the urethral wall 6. Attachment points 131.1 and 131.2 represent optional attachments for the embodiments of FIGS. 12–17 between the sealing member 122 and the stem 112.

Figure 13A:
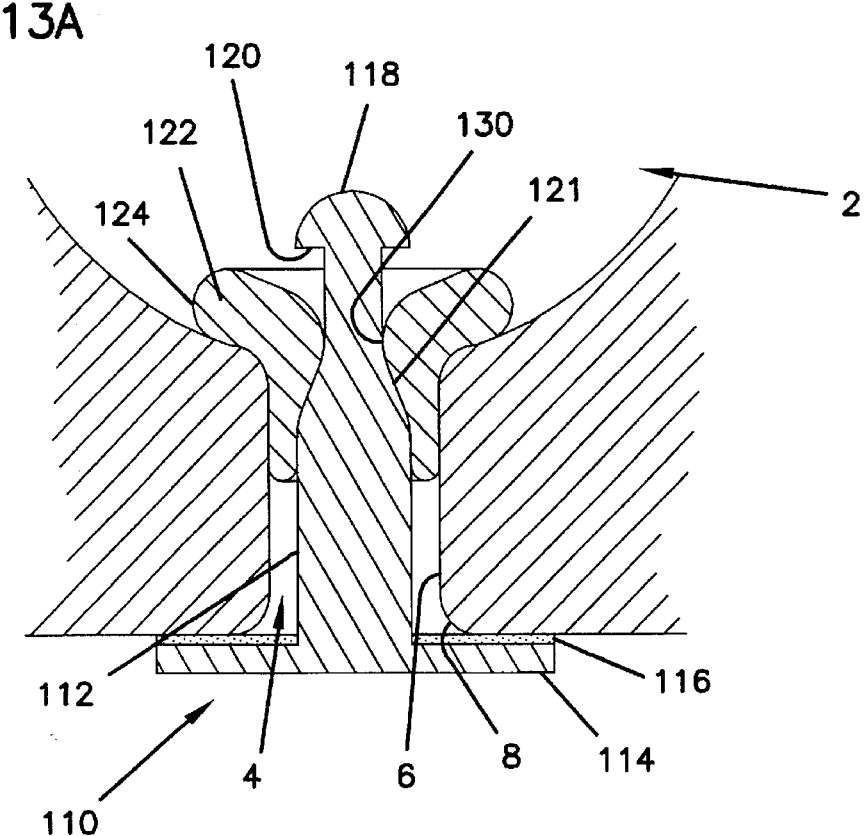
FIG. 13A is a diagrammatic cross-sectional view of an alternative embodiment of a rolling incontinence plug according to the present invention in its fully inserted position in a urethra where a portion of the incontinence plug is shaped to mold the plug into sealing engagement with a bladder neck and a urethral wall.
Figure 13B:
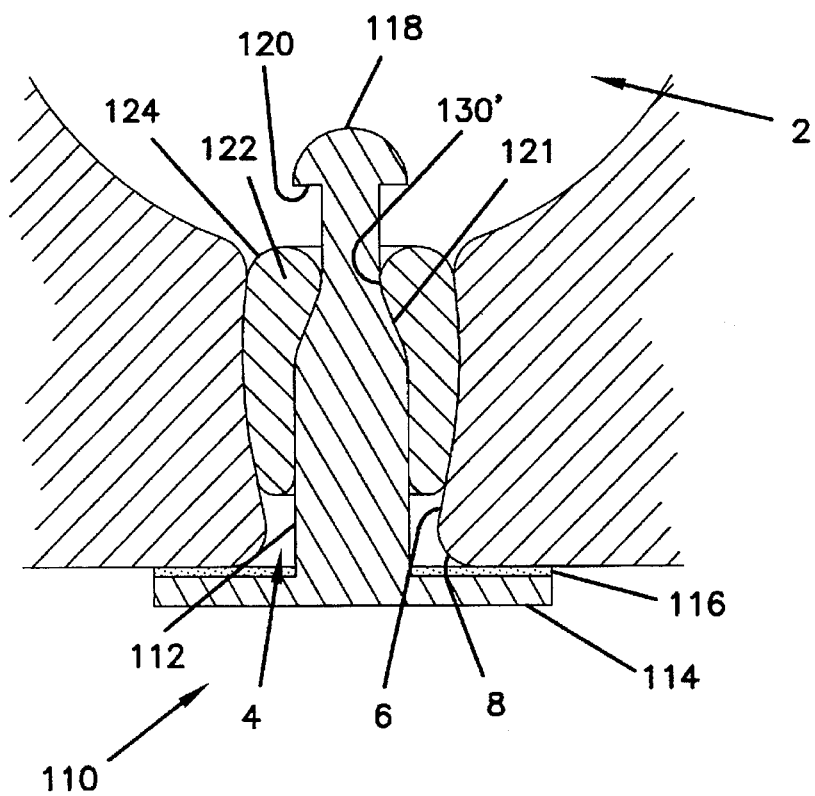
FIG. 13B is a diagrammatic cross-sectional side view of an alternative embodiment of the rolling incontinence plug shown in FIG. 13A where a portion of the incontinence plug is shaped to mold the plug into sealing engagement with the urethral wall.

FIGS. 13A and 13B show alternative embodiments of the invention as described with reference to FIG. 12, with various configurations of the stem 112 to create a leakproof seal between the sealing member 122 and the urethral wall 6 and the bladder 2. FIG. 13A shows a fully inserted plug 110 where the stem 112 tapers outwardly and downwardly toward the flange 114. The diameter of the tapered portion of the stem 112 is greater than the diameter of the distal end of the stem 112. The tapering begins at a location 130 between the proximal and the distal end of the stem 112 such that when the plug 110 is fully inserted, the sealing member 122 is sealably pressed against a portion of the urethral wall 6 and is partially pressed into the bladder 2.

FIG. 13B is a slight modification of the embodiment shown in FIG. 13A in that the stem 112 begins tapering at a location 130' between the distal end and the proximal end such that when the plug 110 is fully inserted, the sealing member 122 is sealably pressed against the urethral wall 6 and is entirely within the urethra 4.

Figure 14A:
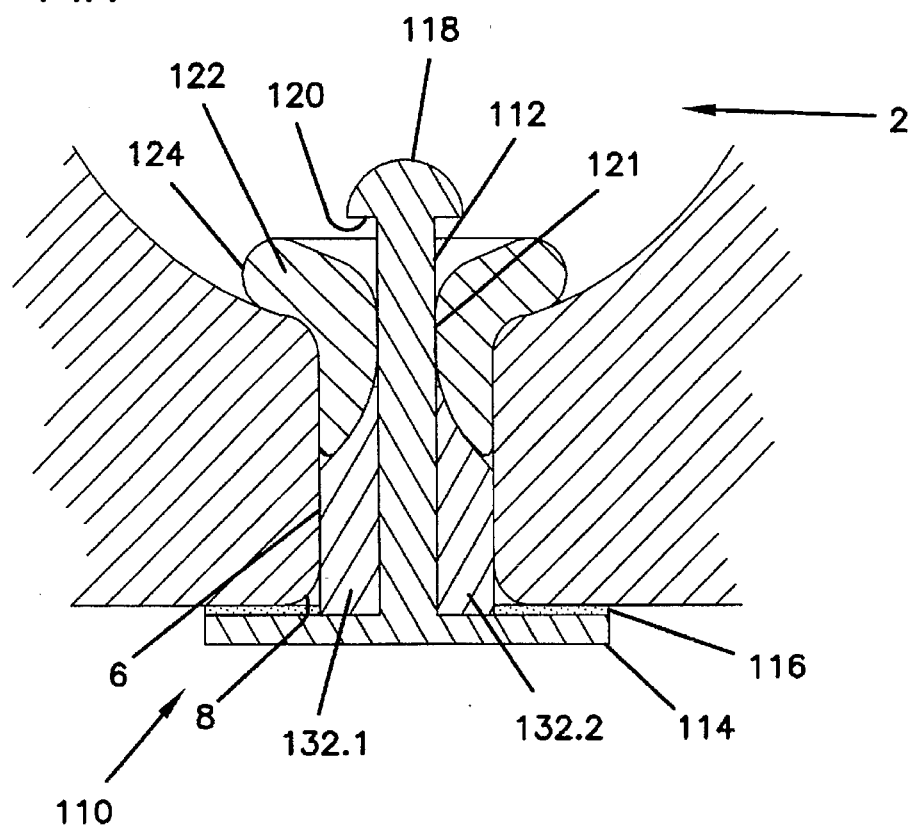
FIG. 14A is a diagrammatic cross-sectional side view of an alternative embodiment of a rolling incontinence plug according to the present invention in its fully inserted position in a urethra where the incontinence plug utilizes sleeve members to mold the incontinence plug into sealing engagement with the bladder neck and a urethral wall.

FIG. 14A shows an alternative embodiment of the invention as described with reference to FIG. 12 using sleeve members 132.1 and 132.2 to sealably press the sealing member 122 against the urethral wall 6 and into the bladder 2, thereby preventing leakage of fluid from the bladder. FIG. 14A shows sleeve members 132.1 and 132.2 extending upwardly from the flange 114 along the outer border of the stem 112. The distal ends of the sleeve members 132.1 and 132.2 taper outwardly (toward the urethral wall 6 when the plug 110 is inserted) and downwardly toward the flange 114. This embodiment presses the sealing member 122 against the urethral wall 6 and into the bladder 2. The sleeve members 132.1 and 132.2 communicate such that combined, they surround the stem 112.

Figure 14B:
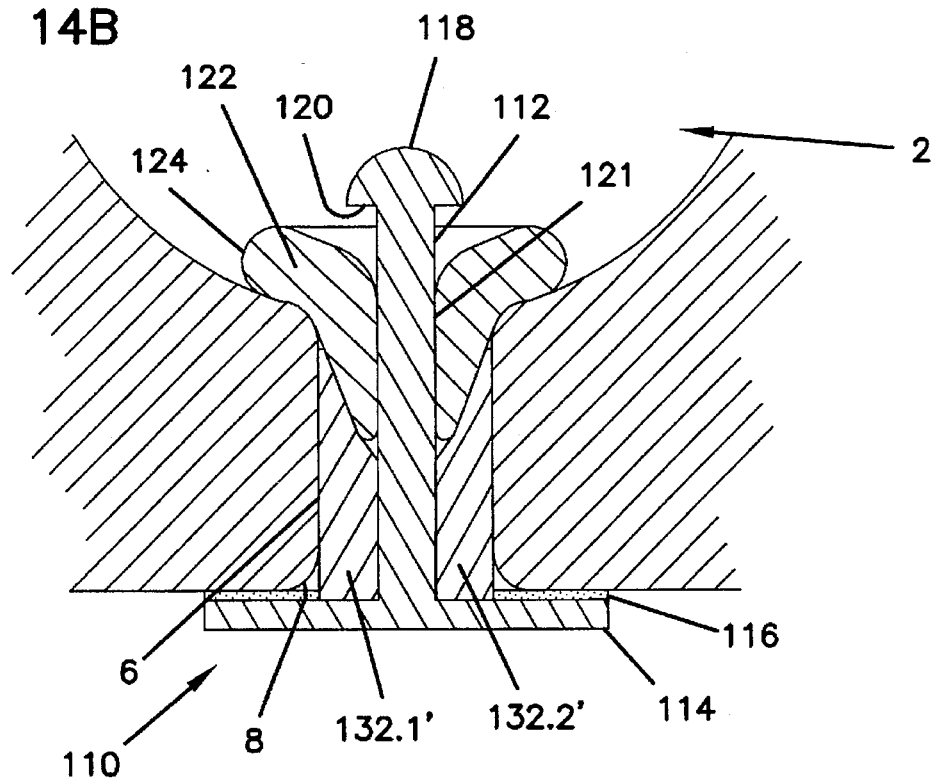
FIG. 14B is a diagrammatic cross-sectional side view of an alternative embodiment of the rolling incontinence plug shown in FIG. 14A, utilizing alternatively shaped sleeve members to mold the incontinence plug into sealing engagement with the bladder neck and the urethral wall.

FIG. 14B shows an alternative shape of sleeve members 132.1 and 132.2 shown in FIG. 14A. Sleeve members 132.1' and 132.2' extend upwardly from the flange 114 spaced from and around the stem 112. Distal ends of the sleeve members 132.1' and 132.2' taper inwardly toward the stem 112 and downwardly toward the flange 114. When fully inserted as shown in FIG. 14B, the sleeve members 132.1' and 132.2' extend along the urethral wall 6 and press the sealing member 122 into the stem 112 and the bladder 2. The various configurations of sleeve members described with reference to FIG. 8 are also applicable to the sleeve members utilized in FIGS. 14A and 14B.

Figure 15:
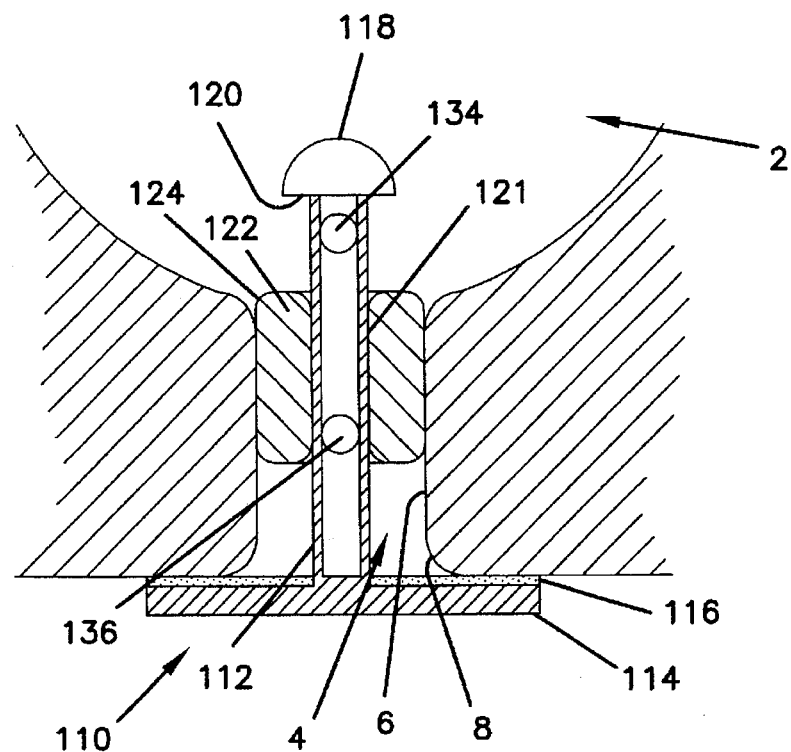
FIG. 15 is a diagrammatic cross-sectional side view of an alternative embodiment of a rolling incontinence plug according to the present invention in its fully inserted position within a urethra where the incontinence plug allows selective depletion of fluids using an inlet port and an outlet port in the plug.

FIG. 15 shows an alternative embodiment of the incontinence plug 110 described with reference to FIG. 12. The plug 110 in FIG. 15 offers the patient the added feature of selectively releasing fluid from the bladder 2 without removing the plug 110. The plug 110 is configured substantially the same as the embodiment shown in FIG. 12. However, the stem 112 must be hollow and has an inlet port 134 near the distal end and an outlet port 136 near the proximal end. The inlet port 134 receives fluid from the bladder 2 and the outlet port 136 releases the fluid received in the inlet port 134. The plug 110 is configured such that when fully inserted as shown in FIG. 15, the sealing member 122 is positioned around the hollow stem 112 to block the outlet port 136. The patient can selectively release fluid by moving the stem 112 and thereby rolling the sealing member 122 such that the sealing member 122 does not block the inlet port 134 or the outlet port 136. This allows fluid to flow out of the outlet port 136. Once the fluid depletion is complete, the patient simply advances the hollow stem 112 into its fully inserted position, causing the sealing member 122 to roll back into the position of blocking the outlet port 136 of the stem 112. It will be obvious to those skilled in the art that the plug 110 could also be configured to allow the sealing member 122 to block the inlet port 134 during a fully inserted position. Movement of the stem 112 would move the sealing member 122 and thereby allow the inlet port 134 to receive fluid from the bladder 2 which would then be released through the outlet port 136.

Figure 16:
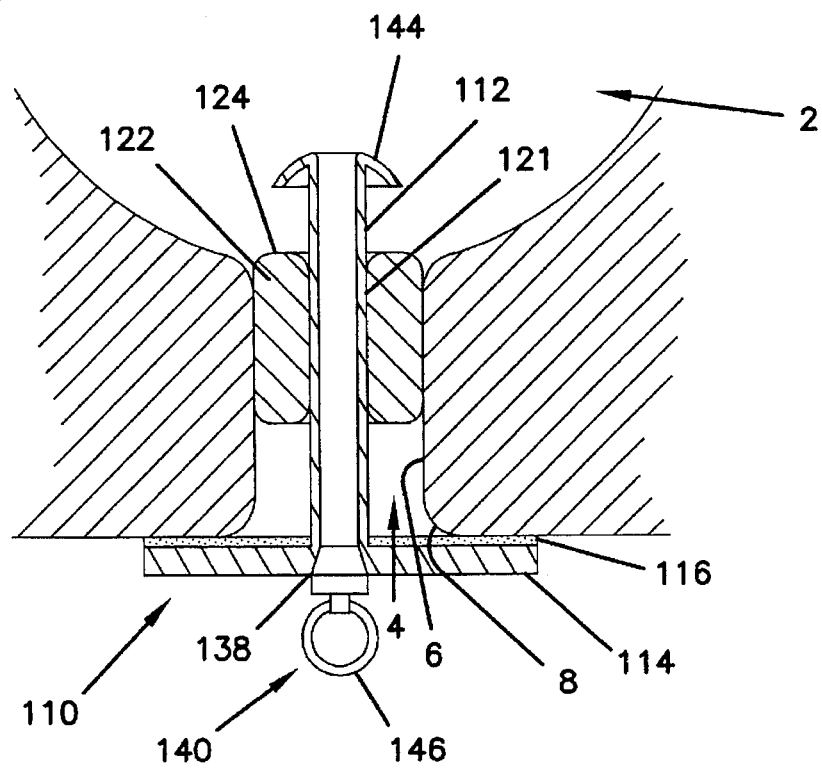
FIG. 16 is a diagrammatic cross-sectional side view of an alternative embodiment of the rolling incontinence plug, similar to that of FIG. 15 where the plug allows selective depletion of fluids, showing an open passageway with a removable blocking plug.

FIG. 16 is an alternative embodiment of the invention in FIG. 12 utilizing the added feature of selective release of fluid from the bladder 2. In the embodiment shown in FIG. 16, the stem 12 is hollow. The flange 114 has an opening 138 where the hollow stem 112 is attached. A blocking plug or valve 140 is inserted into the flange opening 138 to prevent fluid from escaping from the hollow stem 112. The distal end of the hollow stem 112 does not have a dome as shown in previous embodiments. Rather, the distal end is open allowing fluid from the bladder 2 to freely flow into the hollow stem 112. However, the distal end has rounded outwardly extending edges 144, to secure the sealing member 122 on the stem 112. The blocking plug 140 shown in FIG. 16, and its variations, are the same as those described with reference to FIG. 9.

Figure 17:
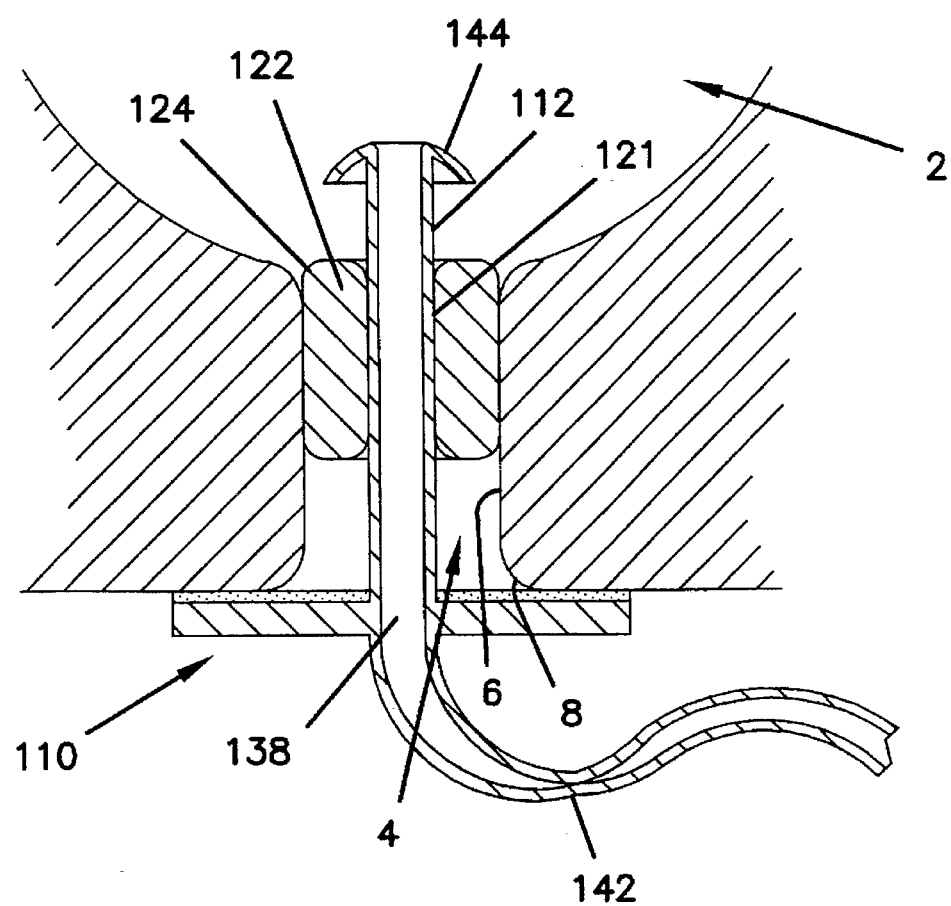
FIG. 17 is a diagrammatic cross-sectional side view of an alternative embodiment of the rolling incontinence plug, similar to that of FIG. 15 where the plug allows selective depletion of fluids, showing a plug extension kinked or otherwise clamped to allow selective depletion of fluid.

FIG. 17 is another embodiment of the invention described in FIG. 16, providing for the selective release of fluid from the bladder 2. In the embodiment shown in FIG. 17, the stem 112 is hollow. The flange 114 has an opening 138 where the hollow stem 112 is attached to the flange 114. A hollow stem extension 142 is connected to the flange opening 138 and extends beyond the flange 114. The stem extension 142 is made of deformable material that can be kinked to prevent leakage of fluid from the hollow stem 112. The patient can selectively un-kink the stem extension to release fluid from the bladder 2 and then kink the stem extension 142 again to prevent leakage from the hollow stem 112. As will be apparent to those skilled in the art, other clamping devices that restrict fluid flow can be utilized with the stem extension 142 to prevent leakage.

With each of the embodiments of the rolling incontinence plug shown and described above, a plug that rolls along the urethral wall in order to reduce trauma and reduce the transportation of pathogens is provided. In addition, the rolling action of the sealing member minimizes discomfort to the patient. Although the invention has been described with reference to the plugs 10 and 110 being used inside a urethra, those skilled in the art will know that the plug can also be effectively utilized in other passageways such as a rectum or vagina to restrict the flow of fluid or other substance. While the invention has been disclosed with preferred embodiments for the purpose of illustration, it will be appreciated that modifications and equivalents of the disclosed concepts may be apparent to those skilled in the art having the benefit of the teachings of the present invention. It is intended that the scope of the present invention not be limited by the specific embodiments shown above but shall include such modifications and equivalents.

What is claimed is:

1. A member for restricting the insertion of an incontinence plug into a urethra at a urethral entrance, said member comprising,
   a flexible peripheral member sized to be placed in a space between a vestibule and labia minora surrounding the urethral entrance with said member conforming to a periphery of said space, and
   connecting means for fixedly connecting said flexible peripheral member to the incontinence plug, said connecting means comprising at least one pliable rib extending radially outward from the incontinence plug, said rib attached to said peripheral member at a first end of said rib and attached to the incontinence plug at a second end of said rib.

2. A member for restricting the insertion of an incontinence plug into a urethra at a urethral entrance, said member comprising,
   a flexible peripheral member sized to be placed in a space between a vestibule and labia minora surrounding the urethral entrance with said member conforming to a periphery of said space, and
   connecting means for fixedly connecting said flexible peripheral member to the incontinence plug, said connecting means comprising a first pliable rib extending radially outward from the incontinence plug and a second pliable rib extending radially outward from the incontinence plug, said first and second pliable ribs attached to said peripheral member at first ends of said ribs and attached to the incontinence plug at second ends of said ribs.

3. A member for restricting the insertion of an incontinence plug into a urethra at a urethral entrance, said member comprising,
   a flexible peripheral member sized to be placed in a space between a vestibule and labia minora surrounding the urethral entrance with said member conforming to a periphery of said space, and
   connecting means for fixedly connecting said flexible peripheral member to the incontinence plug, said connecting means comprising a first pliable rib extending radially outward from the incontinence plug and a second pliable rib extending radially outward from the incontinence plug, said first and second pliable ribs attached to said peripheral member at first ends of said ribs and attached to the incontinence plug at second ends of said ribs,
   wherein said first rib is configured substantially at 180 degrees to said second rib.

4. A member for restricting the insertion of an incontinence plug into a urethra at a urethral entrance, said member comprising,
   a flexible peripheral member sized to be placed in a space between a vestibule and labia minora surrounding the urethral entrance with said member conforming to a periphery of said space, and
   connecting means for fixedly connecting said flexible peripheral member to the incontinence plug said connecting means comprising a substantially planar pliable mass disposed within a planar area defined by said peripheral member, said pliable mass having an outer perimeter in communication with said peripheral member, said outer perimeter attached to said peripheral member, and
   wherein the incontinence plug extends axially through said pliable mass, said pliable mass attached to the incontinence plug.

5. A plug for treating incontinence in human females having qenitalia including a vestibule and labia minora surrounding a urethral entrance, said plug comprising,
   a. means for controlling leakage of a bladder through a urethra, and
   b. a member for anchoring said controlling means at the urethral entrance said member comprising,
      i. a flexible peripheral member sized to be placed in a space between the vestibule and the labia minora with said peripheral member conforming to a periphery of said space, and
      ii. connecting means for fixedly connecting said peripheral member to said controlling means, said connecting means comprising at least one pliable mass disposed within at least a portion of a planar area defined by said peripheral member, one end of said pliable mass attached to said peripheral member and another end of said pliable mass attached to said controlling means.

* * * * *